United States Patent [19]

Santi et al.

[11] Patent Number: 5,753,578
[45] Date of Patent: May 19, 1998

[54] METALLOCENE CATALYST FOR THE (CO) POLYMERIZATION OF α-OLEFINS

[75] Inventors: Roberto Santi; Giampiero Borsotti; Antonio Proto, all of Novara; Liliana Gila, Cameriano, all of Italy; Karel Bujadoux, Lens, France

[73] Assignee: Enichem S.p.A., Milan, Italy

[21] Appl. No.: 667,622

[22] Filed: Jun. 21, 1996

[30] Foreign Application Priority Data

Jul. 6, 1995 [IT] Italy ..................... MI95/A1444

[51] Int. Cl.$^6$ .......................................... C08F 4/64
[52] U.S. Cl. ................... 502/114; 502/117; 502/152; 502/155; 526/127; 526/153; 526/160; 526/348.2; 526/348.5; 556/11; 556/53
[58] Field of Search ..................... 502/114, 117, 502/152, 155; 526/127, 153, 160, 943

[56] References Cited

U.S. PATENT DOCUMENTS 5,529,966  6/1996  Luciani et al. .

OTHER PUBLICATIONS

Han et al. "Ethylene and Propylene Polymerization over Chiral ansa–Dichloro [O–Phenylenedimethylenebis (n5–1–indenyl)]zirconium", Macromolecules, 1995, 28, pp. 4801–4805.

Primary Examiner—David W. Wu
Attorney, Agent, or Firm—Oblon, Spivak, McClelland, Maier & Neustadt, P.C.

[57] ABSTRACT

A catalyst active in the (co)polymerization of α-olefins is obtained by putting the following components in contact with each other:

(i) a "bridged" bis-metallocene derivative of a metal M selected from titanium, zirconium or hafnium, wherein the divalent "bridge" has a rigid structure linked to two $\eta^5$-cyclopentadienyl ring with two methylene groups having a distance from each other of less than 3.5 Å;

(ii) a co-catalyst consisting of an organic derivative of a metal M' selected from boron, aluminium, gallium and tin.

Such a catalyst allows high polymerization rates to be reached and is particularly suitable for high temperature polymerization process and co-polymerization of ethylene with other α-olefins.

29 Claims, 1 Drawing Sheet

METALLOCENE CATALYST FOR THE (CO) POLYMERIZATION OF α-OLEFINS

The present invention relates to a metallocene catalyst for the (co)polymerization of α-olefins.

More specifically, the present invention relates to a metallocene complex of a transition metal and a catalyst suitable for polymerizing or copolymerizing ethylene and/or α-olefins, consisting of the same combined with an organometallic derivative of a metal of group 13 or 14 of the periodic table of elements. The present invention also relates to a method for the preparation of this metallocene complex and the corresponding ligands.

It is generally known in the art that ethylene, or α-olefins in general, can be polymerized by processes at low or medium pressure with catalysts based on a transition metal, generally known as catalysts of the Ziegler-Natta type. A particular group of these catalysts which are active in the polymerization of α-olefins consists of a combination of an organic oxyderivative of aluminium (commonly called aluminoxane) with an $\eta^5$-cyclopentadienyl derivative of a metal normally selected from titanium, zirconium or hafnium (group 4 of the periodic table), also commonly called metallocene, definable in its more general form with the following formula;

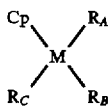

wherein M represents a metal of group IVA of the periodic table of elements, formally in the oxidation state +4, and is preferably titanium or zirconium. $R_A$ and $R_B$ each independently represent a group of an anionic nature such as, for example, a hydride, a halide, a phosphonated or sulfonated anion, an alkyl or alkoxy group, an aryl or aryloxy group, an amide group, a silyl group, etc. Cp independently represents a ligand of the $\eta^5$-cyclopentadienyl type and is generally selected from $\eta^5$-cyclopentadienyl, $\eta^5$-indenyl, $\eta^5$-fluorenyl and their derivatives variously substituted; $R_C$, independently of the nature of the other substituents, can have one of the meanings of either the ligand Cp, or the $R_A$ or $R_B$ groups. "Bridged" metallocenes are also of particular interest in the known art, wherein two Cp groups, the same or different, are bound by a divalent radical normally containing at least one carbon atom and/or heteroatoms. For a known method for the preparation of the above compounds, reference should be made to the description of H. Sinn, W. Kaminsky, in Adv. Organomet. Chem., vol. 18 (1980), page 99 and to U.S. Pat. No. 4,542,199.

These catalysts generally have a high catalytic activity and a certain versatility when applied to the preparation of polyolefins with specific characteristics, especially with respect to the stereochemically control of the polymerization.

The introduction of a "bridged" group allows the two $\eta^5$-rings of the cyclopentadienyl ligand to be held in a fixed position and to modulate the angle between them. This modification leads to the production of polymers with the desired characteristics depending on the catalytic composition and the α-olefin to be polymerized.

One of the advantages of "bridged" catalysts is the capability to give polymers with a high stereospecificity. Whereas the complex $(Ind)_2ZrCl_2$ gives a polypropylene with a low isotactic index [L. Resconi et al. Macromolecules 25, 6814–6817, (1992)], the corresponding catalysts with ethylidene and dimethylsilyl bridges give polypropylene with an isotacticity of 99% and 97% respectively, as indicated for example in German patents DE 3,743,321 and DE 3,443,087.

A second advantage of "bridged" structures is the capacity of inserting a greater quantity of comonomer in the preparation of olefinic copolymers. J. C. W. Chien, in the publication "Journal of Polymer Science, Sec. A, Polymer Chemistry", vol. 29 (1991), pages 1585–1593, asserts that, under the same experimental conditions, the quantity of propylene incorporated in the preparation of ethylene-propylene copolymers is doubled going from $Ind_2ZrCl_2$ to $Et(Ind)_2ZrCl_2$.

A third advantage of "bridged" catalysts is the capacity to give polymers with a high molecular weight at a high temperature and consequently the possibility of using these in plants operating at over 130° C. According to patent application EP-A 344887, the catalyst $Me_2Si(THInd)_2ZrCl_2$ produces, under conditions of high temperature (120°–300° C.) and high pressure (5,000–40,000 psi) an isotactic polypropylene with a $M_W$ of 85,300 and with a tacticity index of 98.6%.

In the publication EP-A 310.734, the above complexes are also used in a mixture to obtain a polymer with a MWD>2 which is consequently easier to process. In "Makromolecu-lare Chemie", vol. 194 (1993), pages 1745–1755, "bridged" complexes are described supported on inorganic substrates ($Al_2O_3$, $MgCl_2$) and used in the presence of trialkylaluminium $AlR_3$, instead of MAO, in the polymerization of propylene, whereas in "Journal of American Chemical Society", vol. 113 (1991), pages 8570–8571 cationic "bridged" complexes are used, which are active in polymerization even without MAO.

Patent and scientific literature on "bridged" catalysts is very vast. The numerous structures studied and claimed are preferably based on Zr and Hf and contain $\eta^5$-cyclopentadienyl (CP), $\eta^5$-indenyl (Ind) or $\eta^5$-fluorenyl (Flu) rings as ligands. Rings of this type also substituted with suitable substituent groups to improve the performance of the catalyst and resulting polymer have been studied. W. Spaleck et al., in "Angew. Chemie, Int. Ed. Eng.", vol. 31(1992), pages 1347–1349, assert that the catalyst $Me_2Si(Ind)_2ZrCl_2$ gives a polypropylene with a higher molecular weight if a methyl substituent is placed on the indenyl ring in position 2, whereas a further substitution with a naphthyl ring in position 4 also increases the yield of polymer and tacticity index ("Organometallics", vol. 13(1994), pages 954–963).

Numerous other examples are cited in patent literature, in European patent applications EP-A 582.194, EP-A 537.130, EP-A 574.370 and EP-A 581.754.

In spite of the numerous advantages with respect to the prior known art, represented by the so-called "classical" Ziegler-Natta catalysts, having an intrinsically heterogeneous nature, also the known catalysts based on metallocenes have some drawbacks such as, for example, the production of polymers with an average molecular weight which is still insufficient for certain applications in which polyolefins with a high or very high molecular weight are required. In addition, also in the case of metallocenes, it is desirable to further improve the stereoselectivity in the polymerization of α-olefins with processes at high temperature and pressure, of about 150°–250° C. and 500–1000 atms.

Another not completely satisfactory aspect of the above catalysts relates to their behaviour in the co-polymerization of ethylene to produce low density polyethylene or olefin elastomers, again with respect to the difficulty in obtaining copolymers with sufficiently high molecular weights, suitable for multiple industrial applications. The necessity is in fact known of operating with substantial quantities of comonomer in order to insert the desired quantity in the copolymer, with a consequent increase in the chain-transfer reaction rate, competitive of the polymerization, and the production of unsatisfactory molecular weights. This disadvantage becomes even more critical in polymerization processes at high temperature in which the chain-transfer reaction is already considerable without the comonomer.

Whereas different types of η$^5$-cyclopentadienyl ligands variously substituted, have been widely studied in the known art, to overcome the above disadvantages and improve the characteristics in relation to the specific applications, there are few publications on the influence, in a polymerization process, of the groups forming the "bridge" between these ligands, which are basically limited, in practice, to the groups —CH$_2$—CH$_2$—, —CMe$_2$— and —SiR$_1$R$_2$— (with R$_1$ and R$_2$ alkyl or phenyl).

The publication "Makromoleculare Chemie, Rapid Comm.", vol. 14 (1993), pages 633–636, describes particular polymerization catalysts based on bis-(η$^5$-cyclopentadienyl) complexes containing a bridge between the two $^5$ ligands consisting of a 1,3-phenylenedimethylene group. These complexes, although capable of polymerizing ethylene in the presence of MAO, still have a limited solubility in aromatic and/or aliphatic hydrocarbons, and a much lower activity than that of the more common metallocene complexes, such as, for example Cp$_2$ZrCl$_2$.

Again the publication "Acta Chimica Sinica", vol. 48 (1990), pages 298–301, describes the preparation of several bis-η$^5$-cyclopentadienyl complexes of zirconium and titanium, which contain a phenylenedimethylene bridge between the two cyclopentadienyl ligands. No mention is made however in this publication of the possible use of these complexes in the polymerization of α-olefins.

Taek Kyu Han et al. in the publication "Macromolecules, vol. 28 (Jul. 4, 1995), page 4801", disclose polymerization of ethylene and propylene in the presence of a catalyst based on [o-phenylenedimethylenebis- (η$^5$-1-indenyl)]-zirconiumdichloride and methylalluminoxane (MAO). Although interesting kinetic studies are presented in such a publication, nothing is disclosed on the co-polymerization of ethylene, nor on the (co)polymerization of α-olefins at high temperature and pressure.

The Applicant has now found a new group of catalysts for the (co)polymerization of α-olefins, based on particular metallocene complexes containing rigid "bridged" groups, which can be prepared with simple and convenient synthetic methods. These complexes, in the presence of a suitable co-catalyst are capable of (co)polymerizing α-olefins without the disadvantages mentioned above and giving a polymer with a high yield and molecular weight.

Therefore, a first object of the present invention relates to a process for the preparation of a co-polymer of ethylene and at least one α-olefin having at least 3 carbon atoms, comprising co-polymerizing ethylene and said α-olefin in suspension, solution or gas-phase, at a temperature from 0° to 250° C., and at a pressure of from 1 to 1200 atms, preferably from 50 to 300 atms, in the presence of a catalyst including the following two components put in contact with each other:

i) a metallocene complex having the following formula(I):

wherein:
M represents a metal selected from titanium, zirconium or hafnium;
A' and A" each independently represent an organic group containing an η$^5$-cyclopentadienyl anion co-ordinated to the metal M,
R' and R" each independently represent a group of an anionic nature -linked to the metal M, preferably selected from hydride, halide, a C$_1$–C$_{20}$ alkyl group, a C$_3$–C$_{20}$ alkylsilyl group, a C$_5$–C$_{20}$ cycloalkyl group, a C$_6$–C$_{20}$ aryl group, a C$_1$–C$_{20}$ alkoxyl or thioalkoxyl group, a C$_2$–C$_{20}$ dialkylamide group and a C$_4$–C$_{20}$ alkylsilylamide group;
B represents a divalent organic residue comprising a unsaturated group linked to two —CH$_2$— methylene groups so that they form with this unsaturated group a rigid molecular structure, and their distance in the space is less than 3.5 Å.

(ii) a co-catalyst consisting of an organic derivative of a metal M' selected from boron, aluminium, gallium and tin.

A second object of the present invention relates to a process for the (co)polymerization of α-olefins, comprising polymerizing an α-olefin, or co-polymerizing a mixture of α-olefins, in suspension, solution or gas-phase, at a temperature above 100° C., preferably from 150° to 240° C., and at a pressure of from 1 to 1200 atms, preferably from 100 to 300 atms, in the presence of a catalyst according to the definition given above.

The catalyst for the (co)polymerization of olefins according to the above definition is also an object of the present invention, with the proviso that, when the groups A' and A" are both η$^5$-indenyl (C$_9$H$_7$), the divalent organic residue B is different from ortho-phenylene.

Figure 1:
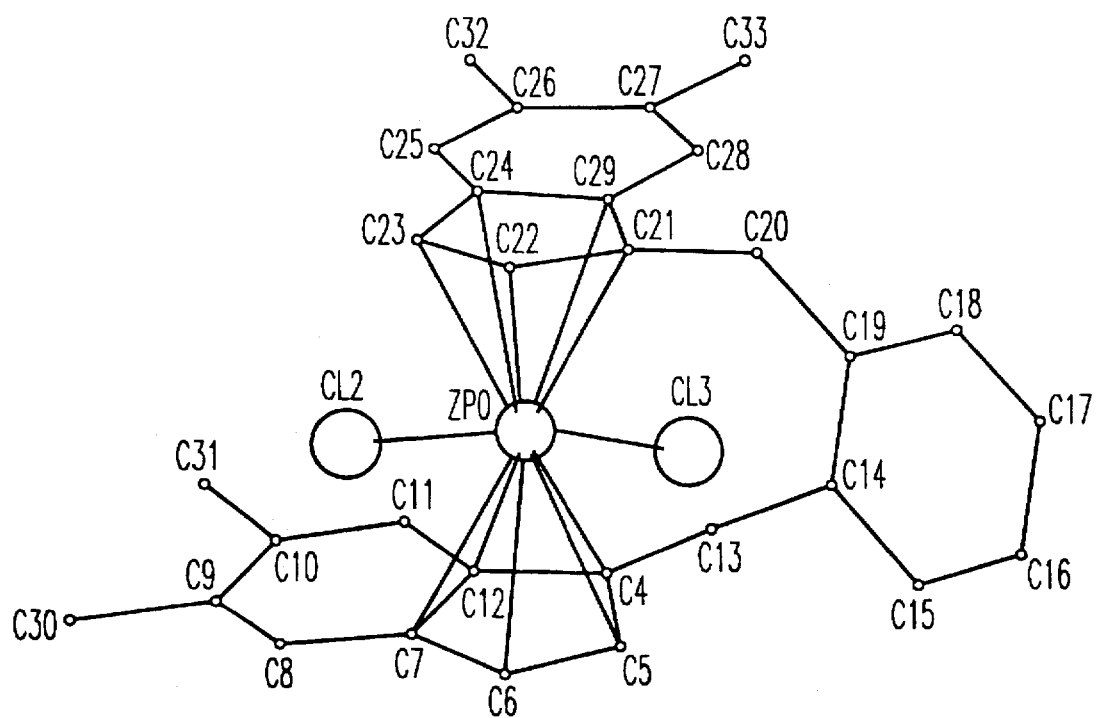
FIG. 1 is a representation of the crystalline structure of claimed metallocene compound.

Other possible objects of the present invention will appear evident in the following description and examples.

The term "rigid molecular structure", as used in the present description and claims refers to structures, possibly inserted in molecular structures of greater dimensions, in which the atoms different from hydrogen or halogen cannot move away from each other without breaking at least one covalent bond in the structure itself, obviously excluding vibrational movements.

In the complexes having formula (I) of the catalysts of the present invention, group B "bridge"-joins the two η$^5$-cyclopentadienyl groups A' and A" giving to the structure of the molecule a particular rigidity. This group B is generally a cyclic or acyclic organic group, containing from 1 to 30 carbon atoms, which can also comprise one or more heteroatoms of non-metals included in groups 14 to 17 of the periodic table of elements, preferably selected from Si, N, O, S, P, Cl, Br and F, more preferably from Si, N, O and Cl. In another preferred form group B is a C$_2$–C$_{20}$ hydrocarbyl group not containing heteroatoms.

According to the previous definition, B comprises an unsaturated group linked to the two methylene groups in formula (I). This unsaturated group can be an olefinically unsaturated group characterized by a double bond such as, for example, a double —C=C— bond, or a —C=N— group containing a heteroatom. This olefinically unsaturated group can be linked to each of the two methylene groups (—CH$_2$—) with each of the two atoms at the ends of the double bond, with the configuration "Z", such as, for example, in the B groups (dimethylene) having the following formulae:

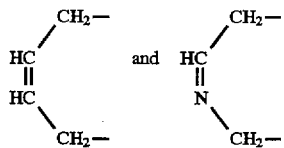

or it can be linked with a single carbon atom, such as for example in the case of the B groups (dimethylene) having the following formulae:

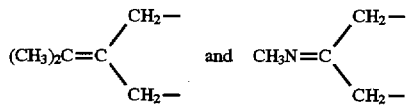

Group B of the present invention can also consist of an ortho-phenylene group or ortho-phenylene group substituted on any of the remaining positions on the ring. The substituent groups are preferably halogen, such as fluorine, chlorine or bromine, a C$_1$–C$_8$ alkyl group such as, for example, methyl, ethyl, butyl, isopropyl, isoamyl, octyl, benzyl, a C$_3$–C$_{12}$ alkylsilyl group such as, for example, trimethylsilyl, triethylsilyl or tributylsilyl, a cycloalkyl group such as cyclopentyl or cyclohexyl, a C$_6$–C$_{10}$ aryl group such as phenyl or toluyl, a C$_1$–C$_8$ alkoxyl group such as, for example, methoxyl, ethoxyl, iso- or sec-butoxyl, or also groups forming a further cycle, saturated or unsaturated, condensed with the main ring. Specific, but non-limiting examples of ortho-phenylene B groups are 2,5-dimethyl-o-phenylene, 3,4-dime-thyl-o-phenylene, 3-ethyl-o-phenylene, 3-octyl-o-phe-nylene, 3,4-difluoro-o-phenylene, 2-methoxy-o-phenylene, 1,2-naphthylene, 2,3-naphthylene, 2,3-phenanthrylene, etc.

Another category of divalent B groups included in the scope of the present invention consists of condensed aromatic groups in which the atoms linked to the two methylene groups of formula (I) are in "peri" position on two adjacent aromatic rings. Groups belonging to this category are, for example, 1,8-naphthalene, 4,5-dimethyl-1,8-naphthalene, 5,6-acenaphthylene, etc.

Excluded however from the scope of the present invention are B groups in which the positions of the two methylene groups of formula (I) are situated at a distance of more than 3.5 Å. Examples of these groups are substituted or non-substituted meta-phenylene groups and "trans" ethylene groups.

According to the present invention, groups R' and R" of formula (I) each independently represent a group of an anionic nature -linked to the metal M. Typical examples of R' and R" are hydride, halide, preferably chloride or bromide, a linear or branched alkyl group such as methyl, ethyl, butyl, isopropyl, isoamyl, octyl, decyl, benzyl, an alkylsilyl group such as, for example, trimethylsilyl, triethylsilyl or tributylsilyl, a cycloalkyl group such as cyclopentyl, cyclohexyl, 4-methylcyclohexyl, an aryl group such as phenyl or toluyl, an alkoxyl or thioalkoxyl group such as methoxyl, ethoxyl, iso- or sec-butoxyl, ethylsulfide, or again, a dialkylamide group such as diethylamide, dibutylamide, or alkylsilylamide group such as bis (trimethylsilyl)amide or ethyltrimethylsilylamide.

According to the present invention, each A' or A" group in formula (I) is an anion containing an η$^5$-cyclopentadienyl ring co-ordinated to the metal M, which formally derives from a molecule of cyclopentadiene, substituted or non-substituted, by the extraction of an H$^+$ ion. The molecular structure and typical electronic and co-ordinative configuration of metallocene complexes of titanium, zirconium or hafnium generally comprising two η$^5$-cyclopentadienyl groups has been widely described in literature and is known to experts in the field.

In the most general form of the present invention, each A' or A" group is linked to a methylene group of the "bridge" B (dimethylene) in formula (I), with any atom of its own structure, which has a suitable valence available for the formation of a covalent bond. In the present invention however, metallocene complexes of formula (I) are preferred in which the methylene group (—CH$_2$—) is linked directly to an atom of the η$^5$-cyclopentadienyl ring of A' or A", more preferably in position 1 or 3, when A' and/or A" consist of anions of the indenyl type.

Typically, each A' or A" group of the above preferred complexes can be represented by the following formula (II):

wherein each substituent R$_1$, R$_2$, R$_3$ and R$_4$ independently represents hydrogen, halogen, preferably F, Cl or Br, a C$_1$–C$_{20}$ aliphatic or aromatic hydrocarbyl group, or a C$_1$–C$_{20}$ hydrocarbyl group substituted with halogen atoms, or a C$_1$–C$_{20}$ hydrocarbyl group comprising one or more heteroatoms of groups 14 to 16 of the periodic table of elements, preferably Si, O, N, S or P, or, wherein any two of the substituents R$_1$, R$_2$, R$_3$ and R$_4$, adjacent to each other, are joined to each other to form a cyclic C$_4$–C$_{20}$ structure, saturated or unsaturated, comprising a bond of the cyclopentadienly ring, this structure optionally containing one or more of the heteroatoms specified above.

Included in the previous formula (II) of preferred A' or A" groups are the known cyclopentadienyl, indenyl or fluorenyl groups, and their derivatives, wherein one or more carbon atoms of the molecular skeleton (included or not included in the cyclopentadienly ring) are substituted with halogen, preferably chlorine or bromine, a linear or branched alkyl group such as methyl, ethyl, butyl, isopropyl, isoamyl, octyl, decyl, benzyl, an alkylsilyl group such as, for example, trimethylsilyl, triethylsilyl or tributylsilyl, a cycloalkyl group such as cyclopentyl, cyclohexyl, 4-methylcyclohexyl, an aryl group such as phenyl or toluyl, an alkoxyl or thioalkoxyl group such as methoxyl, ethoxyl, iso- or sec-butoxyl, ethylsufide, or again, a dialkylamide group such as diethylamide, dibutylamide, or alkylsilylamide, such as bis (trimethylsilyl)amide or ethyltrimethylsilylamide. These A' or A" groups can also be condensed with one or more other aromatic rings as in the case, for example, of 4,5-benzoindenyl. Particularly preferred A groups are indenyl, fluorenyl, 4,5,6,7-tetrahydroindenyl groups and the corresponding methyl-substituted groups.

Examples of preferred compounds having formula (I) for the purposes of the present invention are the compounds listed below, which however do not limit the scope of the present invention in any way.

| | |
|---|---|
| 1,4-Butene-(Ind)$_2$ZrCl$_2$ | o-Xi[(5,6-dimethyl)Ind]$_2$ZrCl$_2$ |
| 1,4-Butene-(Ind)$_2$TiCl$_2$ | o-Xi-[4,7-dimethyl)Ind]$_2$TiBr$_2$ |
| 1,8-Naphth-(Ind)$_2$ZrCl$_2$ | o-Xi-[(4,7-diphenyl)Ind]$_2$ZrMe$_2$ |
| 1,8-Naphth-(Ind)$_2$Zr(NMe$_2$)$_2$ | o-Xi-[(3,4,7-trimethyl)Ind]$_2$ZrCl$_2$ |
| o-Xi-(Ind)$_2$ZrCl$_2$ | o-Xi-[(3-methyl)Ind]$_2$HfCl$_2$ |
| o-Xi-(Flu)$_2$HfCl$_2$ | o-Xi-[(Flu)$_2$ZrBz$_2$ |
| o-Xi-(Ind)$_2$TiCl$_2$ | o-Xi-[(FluInd)Ti(NMe$_2$)$_2$ |
| o-Xi-(THInd)$_2$TiCl$_2$ | o-Xi-[(5,1-dimethyl)Ind]$_2$ZrMe$_2$ |
| o-Xi-[(4,7-dimethyl)Ind]$_2$TiBz$_2$ | o-Xi-[(3-methyl)Ind]$_2$TiCl$_2$ |

The following abbreviations are used in the above formulae: o-Xi=orthoxylylene, 1,8-Naphth=1,8-naphthylenebisdimethylene, Me=methyl, Bz=benzyl, Ind=indenyl, Flu=fluorenyl, THInd=4,5,6,7-tetrahydroindenyl.

Also included in the scope of the present invention are those catalysts comprising two or more complexes having formula (I) mixed with each other. The catalysts of the present invention based on mixtures of complexes can be advantageously used in polymerization when a wider molecular weight distribution of the polyolefins thus produced, is desired.

According to the present invention, the above catalysts for the (co)polymerization of α-olefins can also be supported on inert solids, preferably consisting of oxides of Si and/or Al, such as, for example, silica, alumina or silicoaluminates. The known supporting techniques can be used for supporting these catalysts, normally comprising contact, in a suitable inert liquid medium, between the carrier, optionally activated by heating to temperature higher than 200 C., and one or both of components (i) and (ii) of the catalyst of the present invention. It is not necessary, for the purposes of the present invention for both of the components to be supported, as the complex having formula (I) alone or the organo-oxygenated derivative (i) of Al, Ga or Sn can be present on the surface of the carrier. In the latter case the component which is not present on the surface is subsequently put in contact with the supported component, at the moment of the formation of the active catalyst for polymerization.

The preparation of the above complexes having formula (I) which can be used for the catalysts of the present invention, can be carried out with any of the known methods of organometallic chemistry, starting from a salt of the metal M and a bis-cyclopentadienyl ligand having the desired structure. In the most general case, this ligand has the general formula (III):

$$HA''—CH_2—B—CH_2—A'H \quad\quad (III)$$

wherein A', A" and B have the general meaning specified above for the complexes of formula (I).

The groups A' and A" preferably have the structure of the compounds previously represented in formula (II).

The preparation of the complexes having formula (L) preferably comprise two steps, in the first of which the ligand having formula (III) is reacted with a lithiumalkyl, such as lithiummethyl or lithiumbutyl, in an inert solvent preferably consisting of an aromatic hydrocarbon or an ether, particularly tetrahydrofuran or ethyl ether. The temperature during the reaction is preferably maintained below room temperature to avoid the creation of secondary reactions. At the end of the reaction the corresponding lithium salt of the cyclopentadienyl dianion is obtained.

In the second step, the salt of the cyclopentadienyl dianion is reacted with a salt, preferably a chloride, of the transition metal M, again in an inert organic solvent at a temperature preferably lower than room temperature. At the end of the reaction the complex having formula (I) is separated and purified according to the known methods of organometallic chemistry.

Numerous general methods and details basically relating to the above method, are described in literature, such as, for example, in the publications of D. J. Cardin "Chemistry of Organo Zr and Hf compounds" J. Wiley and Sons Ed., New York (1986); R. Halterman "Chemical Review", vol. 92 (1992) pages 965–994; R. O. Duthaler and A. Hafner "Chemical Review", vol. 92 (1992) pages 807–832.

A particular synthetic method has been found by the Applicant for the preparation of the bis-cyclopentadienyl ligands having formula (III), in which the "bridge" B consists of an unsaturated group containing a double —C=C— bond wherein each unsaturated carbon atom is linked to a different methylene groups (—CH$_2$—), with a "Z" configuration, and each A' and A" group is a cyclopentadienyl anion.

In accordance with this, the method of the present invention comprises the following steps:

(a) forming a solution of an anion A having the previous formula (II) wherein the substituents R$_1$ and R$_2$ are hydrogen and R$_3$ and R$_4$ are groups different from hydrogen and have the general meaning specified above, by contact and reaction, in a suitable inert solvent at temperatures lower than 40° C., of the corresponding neutral compound AH with an alkyl derivative of a metal of the first group of the periodic table, preferably lithium, (b) adding 1,4-dihalobut-2-ine to the solution obtained in step (a) maintained at a temperature of less than −20° C., so that the quantity in moles of the dihalobutine in this solution is always less than half of the quantity in moles of the anion A$^-$ and reacting until the almost complete disappearance of the dihalobutine, (c) subjecting the compound formed in (b), containing a triple carbon-carbon bond, to reduction with a suitable reducing agent until the triple bond is transformed into a double bond optionally substituted.

Such a method particularly can be used for the preparation of compounds of formula (III) wherein each group A' and A" has the above formula (II), wherein the substituents R$_1$ and R$_2$ are hydrogen and R$_3$ and R$_4$ are groups different from hydrogen and have the general meaning specified above. This method, which forms another object of the present invention is preferably used for the preparation of ligands in which R$_3$ and R$_4$ are joined to each other to form a C$_4$–C$_{20}$ cyclic structure optionally containing one or more heteroatoms. These ligands particularly comprise bis-indenyl and bis-4,5,6,7-tetrahydroindenyl structures substituted or non-substituted on the dicyclic skeleton. For these ligands it was previously found that the methods of the type described above led to the formation of the corresponding compound in which the "bridge" B was linked to the cyclopentadienyl ring in a symmetrical position with respect to the substituents R$_3$ and R$_4$ whereas the present new method very simply allows the "bridge" to be obtained linked in an adjacent position to one of these substituents. In the particular case of the indenyl structure the "bridge" is linked in position 1.

The dihalobutine added in step (b) is preferably 1,4-dichlorobut-2-ine, which is a product commercially available.

Preferred inert solvents for the formation of the solution in step (a) are aromatic hydrocarbons or linear or cyclic ethers, particularly tetrahydrofuran.

Preferred alkyl derivatives of lithium are lithium alkyls having from 1 to 6 carbon atoms, particularly lithiumbutyl and lithiummethyl, which are commercially available.

Step (b) is preferably carried out at temperatures of between −20° and −80° C., more preferably between −50° and −70° C., for a time of between 1 hour and 24 hours, more preferably between 8 and 16 hours.

Particularly preferred AH compounds are indene, 4,5,6,7-tetrahydroindene and 1,2-dimethylcyclopentadiene.

As previously defined, the catalyst of the present invention comprises at least two components (i) and (ii), the latter being a co-catalyst consisting of an organo derivative of a metal M' selected from boron, aluminium, gallium and tin.

In a preferred form of embodiment of the present invention, component (ii) is an organo-oxygenated derivative of aluminium, gallium or tin. This can be defined as a compound wherein the metal is linked to at least one oxygen atom and at least one organic R''' group wherein R''' is $C_1$–$C_{15}$ hydrocarbyl, linear or branched R''' is preferably a linear $C_1$–$C_6$ alkyl, more preferably methyl.

According to the present invention, component (ii) is preferably an organo-oxygenated derivative of aluminium which is usually an aluminoxane. As is known, aluminoxanes are compounds containing Al-O-Al bonds, with a varying O/Al ratio, which can be obtained in the art by reaction, under controlled conditions, of an aluminium alkyl, or aluminium alkyl halide, with water or other compounds containing controlled quantities of available water, such as, for example, in the case of aluminium trimethyl, with a salt hydrate, such as aluminium hexahydrate sulfate, copper pentahydrate sulfate and iron pentahydrate sulfate. Aluminoxanes preferably used for the formation of the polymerization catalyst of the present invention are oligo- or polymeric compounds, cyclic and/or linear, characterized by the presence of repetitive units having the formula:

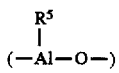

wherein $R^5$ is a $C_1$–$C_4$ alkyl group, preferably methyl.

Each molecule of aluminoxane preferably contains from 4 to 70 repetitive units which may also not be equal to each other, but contain different $R^5$ groups.

These aluminoxanes, and particularly methylaluminoxane are compounds which can be obtained with the known processes of organometallic chemistry, for example by the addition of aluminium trimethyl to a suspension in hexane of aluminium hydrate sulfate.

As well as the above aluminoxanes, also galloxanes (in which gallium is present in the above formulae instead of aluminium) and stannoxanes are comprised in the definition of component (ii) of the present invention, whose use as polymerization co-catalysts of α-olefins in the presence of metallocene complexes is described, for example, for stannoxanes in patents U.S. Pat. No. 5,128,295 and U.S. Pat. No. 5.258.475.

In the (co)polymerization catalysts of ethylene and α-olefins of the present invention the two components (i) and (ii) are used in such proportions that the atomic ratio between the metal M and the metal M' is within the range of 10 to 10000 and preferably between 100 and 5000.

Component (ii) can alternatively be an ionizing compound, capable of transforming the metallocene into a cationic form active in polymerization and becoming a non-coordinating inert anion, according to a known art in the field of metallocene-based catalyst for polymerization of olefins, suitable ionizing compounds for the aims of the present invention are generally bulky derivatives of boron and aluminium, such as for example $B(C_6F_5)_3$, $[Ph_3C]^+$. $[B(C_6F_5)_4]^-$, $[Bu^n{}_3NH]^+.[B(C_6F_5)_4]^-$, $[PhNMe_2H]^+.[B(C_6F_5)_4]^-$, $[Li]^+.[B(C_6F_5)_4]^-$, $[Li]^+$. $[Al(C_6F_5)_4]^{31}$, $[PhNMe_2H]^{30}$. $[B(C_6F_5)_4]^{31}$.

The above compounds are generally used in such a quantity that the molar ratio between the ionizing compound and the catalyst is within the range of 0.3 and 10, preferably from 0.5 to 5.

The ionizing compound can be used alone or combined with MAO or, preferably, with an aluminium trialkyl or alkyl-halogenide having from 1 to 8 carbon atoms in each alkyl residue, most preferably $AlMe_3$, $AlEt_3$, $Al(i-Bu)_3$, in such a quantity that the molar ratio between Al and the catalyst is within the range of 10 and 1000, preferably from 100 to 500. The ionizing compound is preferably used alone when at least one group R' or R" of formula (I) is selected from hydride, an alkyl group, an alkylsilyl group, a cycloalkyl group, an aryl group.

According to the present invention, the procedure with which components (i) and (ii) are put in contact with each other is not critical. In particular the preparation of the polymerization catalyst of the present invention can be carried out by addition of component (i) to component (ii) or viceversa. Moreover, the mixing of the two components can be carried out with satisfactory results either before introducing the α-olefin to be polymerized or in the presence of said α-olefin.

When the ionizing compound is used in combination with an aluminum alkyl, e.g. $AlMe_3$, $AlEt_3$, $Al(i-Bu)_3$, this latter is preferably reacted first with component (i) (the metallocene complex), and the reaction product thereof is made to react with the ionizing compound.

According to the present invention, one or more additives or components can be mixed, and optionally reacted with the catalyst or only one of the two components (i) or (ii), to obtain a catalytic system suitable for satisfying specific requisites in the embodiment. In any case, these catalytic systems should also be considered as being included in the scope of the present invention. Additives or components which can be included in the preparation and/or formulation of the catalyst of the present invention are inert solvents, such as, for example, aliphatic and/or aromatic hydrocarbons, aliphatic and aromatic ethers, weakly co-ordinating additives (Lewis bases) selected, for example, from ethers, tertiary amines and alcohols, halogenating agents such as silicon halides, halogenated hydrocarbons, preferably chlorinated, and the like, and again all the other additional components normally used in the preparation of traditional homogeneous catalysts of the metallocene type for the (co)polymerization of ethylene and α-olefins.

Components (i) and (ii) form the catalyst of the present invention by contact with each other, preferably at temperatures ranging from room temperature to 60° C. and for times varying from 2 minutes to 1 hour.

The catalysts of the present invention can be used with excellent results in basically all the known (co) polymerization processes of α-olefins, such as, for example, processes in suspension, at low, medium or high pressure and at temperatures of between 50° and 240° C.; processes in solution in an inert diluent operating at pressures of between 10 and 150 bars and temperatures of between 120° and 230° C.; or in gas phase, with temperatures generally within the range of 60° to 160° C., at pressures of between 5 and 50 bars. Hydrogen is normally used as molecular weight regulator.

According to a particular aspect of the present invention, the improved catalyst for the (co)polymerization of ethylene and α-olefins is prepared separately by contact of components (i) and (ii), and subsequently introduced into the polymerization environment. The catalyst can be introduced first into the polymerization reactor, followed by the reagent mixture containing the α-olefin or the mixture of α-olefins to be polymerized, or the catalyst can be introduced into the reactor already containing the reagent mixture, or finally, the reagent mixture and the catalyst can be fed contemporaneously into the reactor.

According to another aspect of the present invention, the catalyst is formed in situ in the polymerization reactor, for example by introducing first the organo-oxygenated derivative (ii), subsequently the component containing the metallocene complex having formula (I), and finally feeding the olefinic monomer.

The catalysts of the present invention can be used with excellent results in the polymerization of ethylene to give linear polyethylene and in the copolymerization of ethylene with propylene or higher α-olefins to give copolymers having different characteristics depending on the specific polymerization conditions and the quantity and structure of the α-olefin itself In particular, the present invention also relates to a process for the co-polymerization of ethylene with linear or branched α-olefins having at least 3 carbon atoms, preferably from 3 to 12 carbon atoms, comprising mixing and polymerizing the monomers in the desired proportions, in the presence of a catalyst comprising the previously described components (i) and (ii). An advantageous rate of insertion of the co-monomer (α-olefin) is surprising observed when the complex of formula (I) is used in the catalytic system, thus allowing higher content of co-monomer in the co-polymer.

Particularly preferred for this aim are the complex of formula (I), wherein B is an aromatic divalent group, and both groups A' and A" are selected from $\eta^5$-indenyl, $\eta^5$-4, 5,6,7-tetrahydroindenyl groups, and methyl-substituted derivatives thereof.

The catalyst of the present invention can also be conveniently used for the terpolymerization of ethylene, propylene and a diene to obtain vulcanizable rubbers of the EPDM type. Particularly in the case of the above copolymerization and terpolymerization processes of ethylene, it has been found that the catalysts of the present invention enable the production of polymers having higher average molecular weights than the traditional metallocene catalysts, under the same polymerization conditions and with the same quantity and type of co-monomer inserted.

The present catalysts can also be advantageously used for the stereoselective polymerization of α-olefins, preferably containing from 3 to 20 carbon atoms, to obtain iso- or syndiotactic polyolefins with a high stereospecificity. The iso- or syndio-tactic orientation basically depends on the structure of the α-olefin which is polymerized. For example it is possible to obtain isotactic polymers of propylene (isotactic polypropylene) and 1-butene (isotactic poly-1-butene), and syndiotactic polymers of styrene and its substituted homologous products. In all cases the stereoselectivity which can be obtained with the catalysts of the present invention is very high, normally over 98%, also in processes carried out at high temperatures of up to 180° C.

The present invention is further described by the following examples, which however are purely illustrative and do not limit the scope of the invention itself The determinations by infra-red spectroscopy were carried out with an FTIR spectrometer model Perkin Elmer 1800.

The characterization by $^1$H-NMR spectroscopy, mentioned in the following examples, was carried out on a nuclear magnetic resonance spectrometer mod. Bruker MSL-200, using CDCl$_3$ as solvent for each sample.

The measurement of the molecular weights was carried out by Gel-Permeation chromatography (GPC). The analyses of the polyethylene (PE) samples were carried out in 1,2,4-trichlorobenzene (stabilized with Santonox) at 135° C. with a WATERS 150-CV chromatograph using a Waters differential refractometer as detector.

The chromatographic separation was obtained with a set of μ-Styragel HT (WATERS) columns of which three with pore dimensions of 103, 104, 105 Å respectively, and two with pore dimensions of 106 Å, establishing a flow rate of the eluant of 1 ml/min.

The data were obtained and processed with Maxima 820 software version 3.30 (Millipore); for the calculation of the number (Mn) and weight (Mw) average molecular weight, the universal calibration principles were applied, selecting polystyrene standards for the calibration with molecular weights within the range of 6,500,000–2,000.

The determination of the structures by X-rays was carried out with the known methods.

During the preparations described in the examples the commercial reagents listed below were used:

| | |
|---|---|
| Methyllithium (MeLi) 1.6M in diethyl ether | ALDRICH |
| Butyllithium (BuLi) 2.5M in hexane | ALDRICH |
| α,α'-dibromo-o-xylene | JANSSEN |
| 1,8-bis-(bromomethyl)naphthalene | ALDRICH |
| Zirconium tetrachloride (ZrCl$_4$) | FLUKA |
| Indene | FLUKA |
| 1,4-dichloro-but-2-ine | ALDRICH |
| Methylalumoxane (MAO) 1.57M in toluene | WITCO |

The reagents and/or solvents used and not indicated above are those commonly used and are sold by the usual commercial operators specialized in the field.

EXAMPLE 1

Synthesis of o-xylene-αα'-bis-($\eta^5$-1-indenyl) zirconiumdichloride

1) Synthesis of α,α'-bis(1-indenyl)-o-xylene 70 ml (0.175 moles) of lithium butyl 2.5M in hexane are added, over a period of about 20 minutes, to a solution of 25 g (0.215 moles) of indene in 100 ml of tetrahydrofuran. The mixture is left under stirring for 2 hours, and is then cooled to -10° C. 20 g (0.076 moles) of α,α'-dibromo-o-xylene dissolved in 100 ml of THF are then added, in about 1 hour, so that the temperature of the reaction mixture does not exceed -5° C. At the end, the temperature is left to rise to room temperature, the mixture is hydrolyzed with water and extracted with ethyl ether. The ether extracts, after washing until neutral, and drying on anhydrous sodium sulfate, are evaporated. The residue obtained is purified on a silica gel column using petroleum ether containing 1% of ethyl acetate as eluant. After evaporation of the eluant, 9.5 g of α,α'-bis (1-indenyl)-o-xylene, are obtained, characterized by $^1$H-NMR analysis, with a yield of 26% with respect to the starting dibromo-o-xylene.

$^1$H-NMR (d ppm rel. to TMS): 7.4 (d, 2H), 7.2 (m, 10H), 5.9 (s, 2H), 3.9 (s, 4H), 3.25 (s, 4H).

2) Synthesis of the zirconium complex 22.5 ml (0.036 moles) of methyllithium 1.6M in diethylether are added to a solution of 6 g (0.018 moles) of, '-bis(1-indenyl)-o-xylene in 300 ml of diethyl ether, the mixture being left under stirring for 3 hours. The temperature is then brought to -78° C. and 4.1 g (0.017 moles) of solid Zr°Cl$_4$ are added. The temperature of the mixture is gradually left to rise to room temperature, during the night. A yellow suspension is obtained. It is filtered, washed with 70 ml of diethylether, then with pentane and then dried. The solid is extracted with 2 100 ml portions of methylene chloride. On evaporation of the solvent 9.0 g of solid are obtained which, after crystallization from toluene, gives 3.0 g of o-xylene-α,α'-bis-(η$^5$-1-indenyl)zirconiumdichloride (formula III), characterized by $^1$H-NMR analysis, with a yield of 35% with respect to the starting bis indenyl-o-xylene.

$^1$H-NMR (d ppm rel. to TMS): 4.22 (d, 2H), 4.4 (d 2H), 5.7 (bs, 2H), 6.25 (bs, 2H), 7.2 (m, 6H), 7.5 (m, 4H), 7.6 (d, 2H).

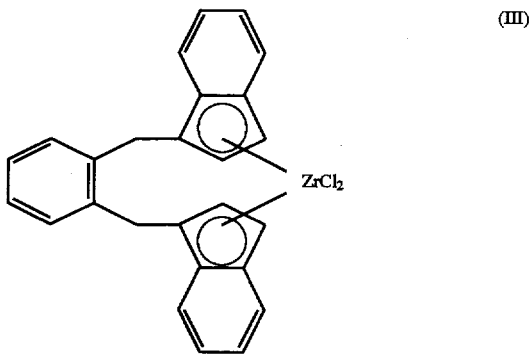

(III)

EXAMPLE 2

Synthesis of [o-xylene-α,α'-bis-(η$^5$-(4,7-dimethyl)-1-(indenyl)]-zirconiumdichloride 1) Synthesis of α,α'-bis-(4,7-dimethyl-indenyl)-o-xylene 60 ml (0.145 moles of butylithium 2.5M in hexane, are slowly added to a solution of 21 g (0.145 moles) of 4,7-dimethylindene in 200 ml of THF, the temperature being maintained at 20°–25° C. At the end of the addition the mixture is kept under stirring for 3 hours. The temperature is then brought to –70° C. and 16.5 g (0.0625 moles) of α,α'-dibromo-o-xylene dissolved in 75 ml of THF are added, under stirring, in such a way that the temperature does not exceed –65° C. At the end the mixture is left under stirring for a night leaving the temperature to rise to room temperature. The reaction mass is hydrolyzed with water and extracted with methylene chloride. The organic extract is washed with water and anhydrified on anhydrous sodium sulfate. After evaporation of the solvent, the residue obtained is treated with petroleum ether, filtered and, after several washings with petroleum ether, the solid obtained is dried under vacuum.

17 g of a slightly yellow solid are obtained which is dissolved in a liter of boiling heptane containing active carbon and filtered, while still hot, on celite. On cooling, a white crystalline solid is separated which is filtered, washed with petroleum ether and dried. 14 g of pure product are obtained which, after characterization by $^1$H-NMR, proves to be α,α'-bis-(4,7-dimethyl-1-indene)-o-xylene, with a yield of 57.4% with respect to the starting dibromo-o-xylene.

$^1$H-NMR (d ppm rel. to TMS): 2.35 (s, 6H, Me), 2.42 (s, 6H, Me), 3.20 (bs, 4H), 4.12 (bs, 4H), 5.95 (bs, 2H), 6.95 (s, 4H), 7.20 (s, 4H).

2) Synthesis of zirconium complex 19 ml of MeLi 1.6M in ethyl ether are added, at room temperature, to a suspension of 5.85 g (0.015 moles) of α,α'-bis-(4,7-dimethyl-1-indenyl)-o-xylene in 250 ml of ethyl ether. The mixture is left under stirring for a night. A dense, white suspension is formed. The suspension is cooled to –70° C. and 3.6 g (0.0156 moles) of zirconium tetrachloride are added. The temperature is left to rise to room temperature in about 2 hours. A yellow suspension is formed which is maintained under stirring for another hour, is then filtered and washed first with ethyl ether and then with pentane. The solid is suspended in 200 ml of methylene chloride and filtered. The residue remaining on the filter is treated again with 150 ml of methylene chloride, filtered and the liquid added to the previous liquid. The yellow solution obtained, after evaporation of the solvent, gives 8.0 g of raw residue. This is recrystallized from hot methylene chloride. The solid obtained is washed with a small amount of methylene chloride then with pentane and dried under vacuum 4.0 g of pure product are obtained which, after characterization by $^1$H-NMR, proves to be [o-xylene-α,α'-bis-($^5$-(4,7-dimethyl)-1-indenyl)]zirconium-dichloride (formula IV), with a yield of 48.5% with respect to the starting bis-(4,7-dimethyl-1-indenyl)-o-xylene.

$^1$H-NMR (d ppm rel. to TMS): 2.46 (s, 6H, CH$_3$(a) or CH$_3$(b)), 2.61 (s, 6H, CH$_3$(b) or CH$_3$(a)), 4.20 (d, 2H, Ha (Hb), J(Ha–Hb)=16 Hz), 4.52 (d, 2H, Hb(Ha), J(Ha–Hb)=16 Hz), 5.88 (d, 2H, Hc(Hd), J(Hc–Hd)=4 Hz), 5.96 (d, 2H, Hd(Hc), J(Hd–Hc)=4 Hz), 6.78 (d, 2H, He(Hf), J(He–Hf)=8 Hz), 6.88 (d, 2H, Hf(He), J(Hf–He)=8 Hz), 7.42 (m, 4H, Hf+Hg).

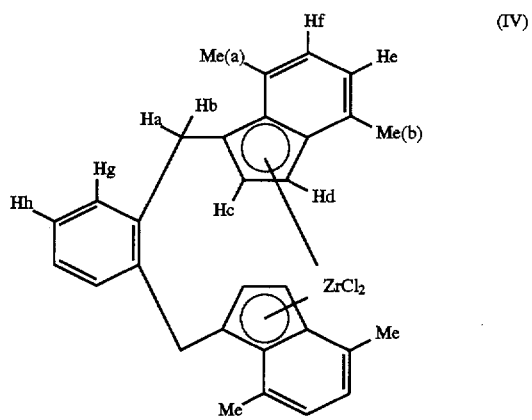

(IV)

EXAMPLE 3

Synthesis of [naphthalene-1,8-bis-(η$^5$-1-indenylmethyl)]zirconiumdichloride

1) Synthesis of 1,8-bis-(1-indenylmethyl)naphthalene 60 ml (0.150 moles) of BuLi 2.5M in hexane are added, at room temperature in about 30 minutes, to a solution of 18 g (0.155 moles) of indene in 200 ml of THF. At the end of the addition, the mixture is left under stirring for 3 hours. The solution is cooled to –70° C. and 18.5 g (0.059 moles) of 1,8-bis-(bromomethyl)naphthalene dissolved in 100 ml of THF, are added in about 1 hour so that the temperature of the reaction mixture does not exceed –65° C. The temperature is then left to rise to room temperature during a night. The reaction mass is poured into water and extracted with ethyl ether. The ether extract is washed and anhydrified on anhydrous sodium sulfate. On evaporation of the solvent a solid residue is obtained which is purified as described in paragraph 1 of example 2 above.

At the end 15.5 g of a pure white solid are obtained which, after characterization by $^1$H-NMR, proves to be 1,8-bis(1-indenylmethyl)naphthalene, with a yield of 68% with respect to the starting 1,8-bis-(bromomethyl)naphthalene.

¹H-NMR (d ppm rel. to TMS): 3.30 (brs, 4H), 4.20 (brs, 4H), 5.6 (brs, 2H), 7.0 (dd, 2H), 7.15–7.6 (m, 10H), 7.9 (dd, 2H).

2) Synthesis of the zirconium complex 19 ml (30.4×10⁻³ moles) of MeLi 1.6M in hexane are added, at room temperature, to a suspension of 5.8 g (15×10⁻³ moles) of 1,8-bis-(1-indenylmethyl)-naphthalene in 200 ml of diethyl ether. The suspended solid completely dissolves and an orange solid then precipitates. The mixture is left under stirring for 3 hours, is then cooled to –70° C. and 3.9 g(16.6×10⁻³ moles) of ZrCl₄ are added. The temperature is left to rise to room temperature during a night, maintaining the mixture under stirring, it is then filtered and a yellow solid is obtained which is extracted with methylene chloride. 7.1 g of raw product are obtained from the extracts, on evaporation of the solvent, which is washed with 30 ml of methylene chloride and subsequently with pentane. After drying 1.5 g (26% yield) of pure product are obtained which, after characterization by ¹H-NMR, proves to be [naphthalene-1,8-bis-(η⁵-1-indenylmethyl)]zirconiumdichloride (formula V), with a yield of 26% with respect to the starting 1,8-bis-(1-indenylmethyl)naphthalene.

¹H-NMR (d ppm rel. to TMS): 4.50 (d, 1H, J=16 Hz), 4.69 (d, 1H, J=16 Hz), 5.32 (d, 1H), 5.42 (d, 1H), 5.81 (d, 1H, J=4 Hz), 5.97 (dd, 1H, J1=4 Hz, J2=2 Hz), 6.57 (m, 2H), 6.91 (dt, 1H, J1=6 Hz, J2=2 Hz), 7.02 (dt, 1H, J1=6 Hz, J2=2 Hz), 7.25–7.29 (m, 2H), 7.39–7.59 (m, 6H), 7.77 (dd, 1H, J1=7 Hz, J2=1.5 Hz), 7.86–8.01 (m, 3H).

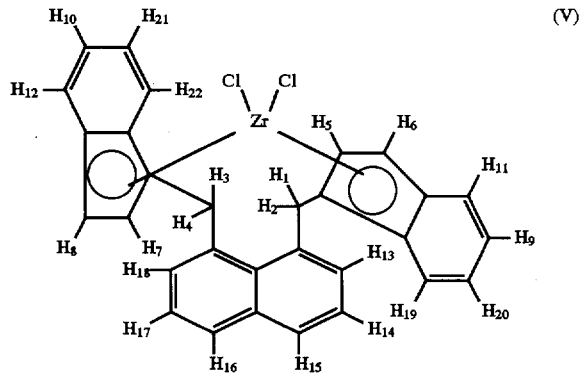

(V)

EXAMPLE 4

Synthesis of o-xylene-α,α'-bis-[-η⁵-(4,7-diphenyl)-1-indenyl]zirconiumdichloride 1) Synthesis of o-xylene-α,α'-bis-(4,7-diphenyl-1-indene)

28 ml (0.070 moles) of BuLi 2.5M in hexane are added, at room temperature, to a solution of 18.75 g (0.070 moles) of 4,7-diphenylindene in 200 ml of THF. At the end of the addition, the mixture is left under stirring for 3 hours and is then cooled to –70° C. 8.7 g (0.033 moles) of α,α'-dibromo-o-xylene dissolved in 70 ml of THF, are added. The temperature is left to rise to room temperature during a night, the mixture being maintained under stirring. The mixture is then hydrolyzed with water and extracted with ethyl ether. After evaporation of the solvent, a foamy solid is obtained from the extracts which is crystallized from 500 ml of boiling heptane 15.4 g of a pure solid are obtained which, after characterization by ¹H-NMR, proves to be o-xylene-α,α'-bis-(4,7-diphenyl-1-indene), with a yield of 73% with respect to the starting α,α'-di-bromo-o-xylene.

¹H-NMR (d ppm rel. to TMS): 1.70 (t, 3H), 2.70 (dd, 2H), 4.20 (dd, 2H), 6.25 (dd, 2H), 7.0–7.7 (m, 30H).

2) Synthesis of zirconium complex 13 ml (0.021 moles) of MeLi 1.6M in diethyl ether are added, at room temperature, to a solution of 6.4 g (0.01 moles) of o-xylene-α,α'-bis-(4,7-diphenyl-1-indene) in 300 ml of ethyl ether. The mixture is then cooled to –70° C. and 3.0 g (0.0128 moles) of zirconium tetrachloride are added. The temperature is left to rise to room temperature and the stirring is maintained for a further 3 hours. The reaction mixture is filtered and the solid obtained is washed with 150 ml of diethyl ether and extracted with methylene chloride, filtering any possible solid residues left in suspension. The volume of the extracts is reduced to 15–20 ml by evaporation of the solvent, obtaining a yellow solid which is filtered and then washed first with 3–4 ml of methylene chloride, then with pentane, and finally dried. 4.1 g of pure product are obtained which, after characterization by ¹H-NMR, proves to be o-xylene-α,α'-bis-[η⁵-(4,7-diphenyl)-1-indenyl]zirconium-dichloride (formula VI), with a yield of 50% with respect to the starting o-xylene-α,α'-bis-(4,7-diphenyl-1-indene).

¹H-NMR (d ppm rel. to TMS): 3.20 (d, 2H, J=16 Hz, Ha(Hb)), 3.45 (d, 2H, J=16 Hz, Hb(Ha)), 5.81 (d, 2H, J=3.2 Hz, Hc(Hd)), 6.36(d, 2H, J=3.2 Hz, Hd(Hc)), 7.1–7.65(m, 28H, Ar).

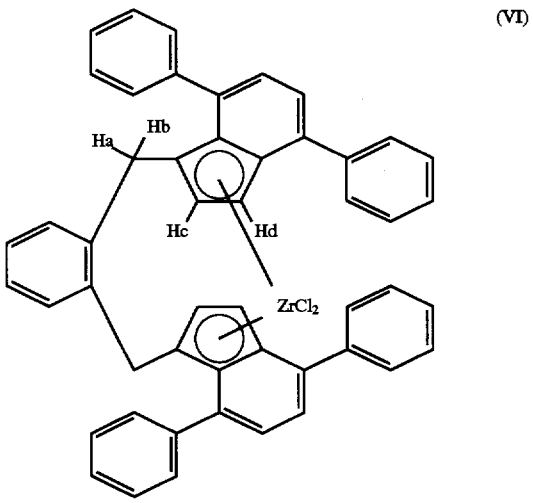

(VI)

EXAMPLE 5

Synthesis of o-xylene-α,α'-bis-[η⁵-1-(3-methyl)indenyl)]zirconiumdichloride

1) Synthesis of 1-methylindene 86 ml (0.215 moles) of BuLi 2.5M in hexane, are added, over a period of about 20 minutes at room temperature, to a solution of 25 g (0.215 moles) of indene in 150 ml of THF. The mixture is kept under stirring for 2 hours and then cooled to –70° C. 14 ml of methyl iodide dissolved in 50 ml of THF are added over a period of about 1 hour. The temperature is then left to rise to room temperature, maintaining the mixture under stirring. The mixture is hydrolyzed with water and extracted with ethyl ether. The extracts are washed until neutral and anhydrified on anhydrous sodium sulfate. After evaporation of the solvent, a residue is obtained which is purified by distillation. 16.5 g of pure product are obtained which, after characterization by ¹H-NMR, proves to be 1-methylindene with a yield of 58% with respect to the starting indene.

2) Synthesis of o-xylene-α,α'-bis-[1-(3-methyl)indene]

52 ml (0.130 moles) of BuLi 2.5M in hexane are added, at room temperature, to a solution of 16.5 g (0.127 moles) of 1-methylindene prepared as described above, in 200 ml of THF. At the end of the addition the mixture is left under stirring for 3 hours and is then cooled to −70° C. 15 g (0.0568 moles) of α,α'-dibromo-o-xylene dissolved in 100 ml of THF are added and the temperature is left to rise to room temperature for a night, the mixture being maintained under stirring. The mixture is hydrolyzed with water and extracted with ethyl ether. After evaporation of the solvent, a solid is obtained from the extracts which is chromatographed on a silica gel column using petroleum ether containing 2% of ethyl acetate as eluant. 15.0 g of pure product are obtained which, after characterization by $^1$H-NMR, proves to be o-xylene-α,α'-bis-[1-(3-methyl)indene], with a yield of 73% with respect to the starting α,α'-dibromo-o-xylene.

$^1$H-NMR (d ppm rel. to TMS): 2.15 (m, 6H), 2.7 (m, 2H), 3.2 (m, 2H), 3.7 (m, 2H), 6.1 (m, 2H), 7.1–7.5 (m, 12H).

3) Synthesis of the zirconium complex 19 ml (0.03 moles) of MeLi 1.6M in diethyl ether are added, at room temperature, to a solution of 5.43 g (0.015 moles) of o-xylene-α,α'-bis-[1-(3-(methyl) indene] in 250 ml of diethyl ether. The reaction takes place very slowly, with the formation of a precipitate. The mixture is left under stirring for a night. It is then cooled to −70° C. and 3.5 g (0.015 moles) of zirconium tetrachloride are added. The temperature is left to rise to room temperature and the stirring is maintained for a further 3 hours, obtaining a yellow suspension. The reaction mixture is filtered and the solid obtained is washed with diethyl ether and extracted, under heat, with four 100 ml portions of methylene chloride. The volume of the extracts is reduced to about 15 ml by evaporation of the solvent, obtaining a solid which is filtered and then washed first with 5 ml of methylene chloride, then with pentane, and finally dried under vacuum. 1.7 g of pure product are obtained which, after characterization by $^1$H-NMR, proves to be o-xylene-α,α'-bis-[η$^5$-1-(3-methyl) indenyl)]zirconiumdichloride (formula VII), with a yield of 22% with respect to the starting o-xylene-α,α'-bis-[1-(3-methyl)indene].

$^1$H-NMR (d ppm rel. to TMS): 1.95 (s, 6H, Me), 4.22 (d, 2H), 4.37 (d, 2H), 6.05 (bs, 2H), 7.05–7.6 (m, 12H).

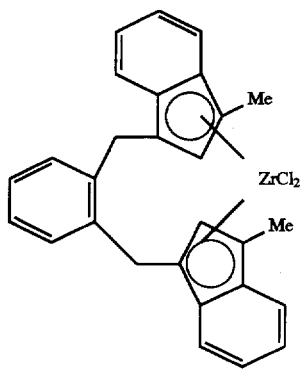

(VII)

EXAMPLE 6

Synthesis of [Z-2-butene-1,4-bis-(η$^5$-1-indenyl)]-zirconiumdichloride

1) Synthesis of 1,4-bis-(1-indenyl)but-2-ine 80 ml (0.20 moles) of BuLi 2.5M in hexane are added, at room temperature, to a solution of 25 g (0.215 moles) of indene in 200 ml of THF. At the end of the addition, the mixture is left under stirring for 3 hours. It is then cooled to −70° C. and 11.5 g (0.094 moles) of 1,4-dichlorobut-2-ine dissolved in 50 ml of THF are added. The reaction mixture is left to rise to room temperature and is maintained under stirring for a night. The mixture is poured into water and is extracted with petroleum ether containing 10–20% of diethyl ether. The mixture is neutralized and the organic extract is dried on anhydrous sodium sulfate. After evaporation of the solvent and after chromatography on a silical gel column with petroleum ether containing 10% of methylene chloride as eluant, 20 g of practically pure 1,4-bis-(1-indenyl)but-2-ine are obtained with a yield of 75% with respect to the starting dichlorobutine.

2) Synthesis of 1,4-bis-(1-indenyl)-Z-but-2-ene

A solution is prepared of 20 g (0.0532 moles) of 1,4-bis-(1-indenyl)-but-2-ine in 200 ml of pyridine. The alkyne is then hydrogenated with hydrogen at 1 atm., in the presence of 1.0 g of Pd on BaSO$_4$ (ALDRICH). After 3 hours the absorption of hydrogen stops. The reddish solution is filtered, diluted with water and extracted with diethyl ether. The extract, after evaporation of the solvent, is purified by chromatography on a silica gel column with petroleum ether as eluant. 17 g of 1,4-bis-(1-indenyl)-Z-but-2-ene are obtained with a yield of 85%.

3) Synthesis of the zirconium complex of ZrCl$_4$ 19 ml (0.0304 moles) of MeLi 1.6M in diethyl ether are added, at room temperature, to a solution of 4.26 g (0.015 moles) of 1,4-bis-(1-indenyl)-Z-but-2-ene in 250 ml of diethyl ether. After about 1 hour a red solution is formed which, after about another hour, becomes yellow. The mixture is left under stirring for two hours, is then cooled to −70° C. and 3.6 g (0.0154 moles) of zirconium tetrachloride are added. The temperature is left to rise to room temperature and a yellow suspension is obtained. The stirring is maintained for a further 1 hour, the suspension is filtered and the yellow solid obtained is washed with diethyl ether. This is then extracted with four 150 ml portions of methylene chloride. The extracts are joined and reduced to a volume of 15–20 ml by evaporation of the solvent. A solid residue is formed which is filtered, washed first with 5 ml of methylene chloride, then with pentane, and then dried under vacuum obtaining 1.0 g of pure product which, after characterization by $^1$H-NMR, proves to be [Z-2-butene-1,4-bis(η$^5$-1-indenyl)]zirconiumdichloride (formula VIII), with a yield of 15% with respect to the starting 1,4-bis-(1-indenyl)-Z-but-2-ene.

$^1$H-NMR (d ppm rel. to TMS): 3.59 (dq, 2H, J1=8.0 Hz, J2=16 Hz), 3.75 (dq, 2H, J1=8.0 Hz, J2=16 Hz), 5.76 (dd, 2H, J1=8.0 Hz, J2=3.4 Hz) 6.38 (d 2H), 6.42 (m, 2H), 7.19 (dq, 2H, J1=7.28 Hz, J2=1.0 Hz), 7.39 (dq, 2H, J1=7.28 Hz, J2=1.0 Hz), 7.62 (td, 2H, J1=8.7 Hz, J2=1.0 Hz), 7.71 (dd, 2H, J1=8.7 Hz, J2=0.9 Hz).

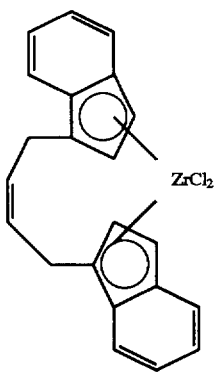

(VIII)

EXAMPLE 7

Synthesis of o-xylene-α,α'-bis-[η⁵-(5,6-dimethyl)-1-indenyl]-zirconiumdichloride 1) Synthesis of: α,α'-bis-(5,6-dimethyl-1-indenyl)-o-xylene 18.5 ml (0.0462 moles) of BuLi 2.5M in hexane are slowly added to a solution of 6.6 g (0.0458 moles) of 5,6-dimethylindene in 150 ml of THF, the temperature being maintained at 20°–25° C. At the end of the addition the stirring is maintained for 3 hours. The temperature is brought to −70° C. and 6.0 g (0.0227 moles) of α,α'-dibromo-o-xylene dissolved in 50 ml of THF are added, over a period of about 1 hour, operating so that the temperature of the mixture does not exceed −65° C. The mixture is left under stirring for a night and the temperature is left to rise to room temperature. The reaction mass is hydrolyzed with water and extracted with diethyl ether. The organic extract is washed with water and anhydrified on anhydrous sodium sulfate. After evaporation of the solvent, the residue obtained is purified on a silica gel column using petroleum ether as eluant. 7.0 g of semisolid product are obtained which are treated with cold pentane and then filtered. 4.5 g of product are obtained (25% yield) which, after characterization by ¹H-NMR, proves to consist of a mixture of isomers of α,α'-bis-[5,6-dimethyl- 1-indenyl)-o-xylene, with a yield of 25% with respect to the starting α,α'-dibromo-o-xylene.

¹H-NMR (d ppm rel. to TMS): 2.27 (s, 6H), 2.32 (s, 6H), 3.26 (br, 3H), 3.65 (m, 1H), 3.9 (m, 2H), 5.87 (m, 1H), 6.35 (m), 6.75 (m), 7.0–7.4 (m, 8H).

2) Synthesis of the zirconium complex 15 ml (0.024 moles) of MeLi 1.6M in ethyl ether are added, at room temperature, to a suspension of 4.5 g (0.0115 moles) of α,α'-bis(5,6-dimethyl-1-indenyl)o-xylene in 250 ml of diethyl ether. After a night under stirring, a dense, white suspension is formed. It is cooled to −70° C. and 3.3 g (0.0141 moles) of zirconium tetrachloride are added. The temperature is brought to room temperature in about 2 hours and the suspension is left under stirring for a further hour, obtaining a yellow suspension which is then filtered and washed first with 100 ml of diethyl ether and then with pentane. The solid obtained is suspended in 200 ml of methylene chloride and filtered. The residue remaining on the filter is treated again with 300 ml of methylene chloride. The two liquid fractions obtained from the filtration are joined and concentrated to a volume of 20–25 ml. The solid which is separated is filtered and washed first with about 5 ml of methylene chloride, and then with pentane. After drying under vacuum, 2.2 g (35% yield) of pure product are obtained which, after characterization by ¹H-NMR, proves to consist of o-xylene-α,α'-bis-[η⁵-(5,6-dimethyl)-1-indenyl]-zirconiumdichloride (formula IX), with a yield of 35% with respect to the starting α,α'-bis-(5,6-dimethyl-1-indenyl)-o-xylene.

¹H-NMR (d ppm rel. to TMS): 2.29 (s, 6H, CH3), 2.34 (s, 6H, CH3), 4.17 (d, 2H, j=16 Hz), 5.57 (d,br, 2H, J=2Hz), 6.12 (br, 2H), 7.16 (br, 2H), 7.33 (s, 2H), 7.40–7.48 (m, 4H).

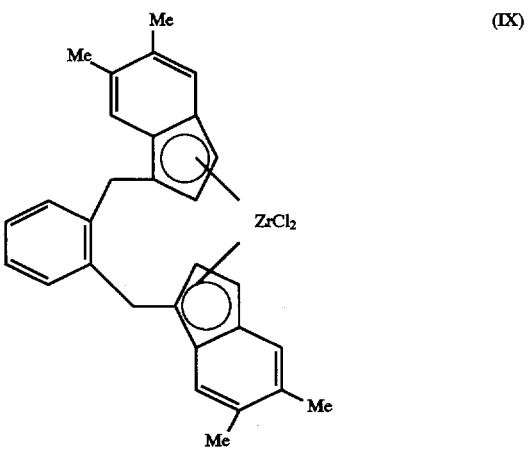

(IX)

The structure of the complex having formula (IX) obtained as described above was determined by X rays, shown in FIG. 1. The X-ray structure confirmed that the distance in the space between the two methylene atoms of the xylylene "bridge" is about 3.1 Å, less than the limit of 3.5 Å claimed in the present invention.

EXAMPLE 8–14 copolymerization of ethylene/1-hexene

Different polymerization tests were carried out corresponding to examples 8 to 14, using the following general procedure:

A solution of the polymerization catalyst (SOL-CAT) of the present invention was prepared separately, by dissolving the desired quantity of complex (prepared according to one of the previous examples 1–7) in 50 ml of toluene, and adding a solution of MAO at 10% in toluene (titer of Al=1.57M) so that the concentration of zirconium is between 50 and 200 mg per liter of solution, and the atomic ratio Al/Zr is equal to about 100. The solution is matured by leaving it under stirring for 30 minutes at room temperature, before being introduced into the polymerization mixture.

470 ml of toluene (previously distilled on metal sodium), 30 ml of 1-hexene (previously distilled on calcium hydride, CaH₂) and 3.18 ml of the above solution of MAO at 10% in toluene (5 mmoles of aluminium) are charged into a BUCHI pressure-resistant 1 liter glass reactor, equipped with a propeller stirrer, thermocouple and heating jacket connected to a thermostat for the temperature control, maintained under vacuum for at least two hours interrupted by three washings with nitrogen. The pressure-resistant reactor is pressurized with ethylene at 2 atms. and is heated to 40° C.

The above reactor is depressurized and the desired quantity of the catalyst solution prepared as described above, is introduced, in a stream of ethylene, so as to have an atomic ratio of 2650 between the zirconium in the complex and the total aluminium contained in the MAO (resulting from the sum of that introduced with the catalyst solution and that introduced directly into the reactor). The reactor is brought again to a pressure of 2 atms with ethylene and the polymerization is carried out for 30 minutes, continuously feeding ethylene to maintain the pressure constant for the whole duration of the test. The polymer is recovered by precipitation in acidified methanol and subsequent washings with acetone. The polymer thus obtained is an ethylene-1-hexene copolymer (LLDPE) which is characterized by measuring the number average molecular weight ($M_n$) and the weight average molecular weight ($M_w$), the molecular weight distribution (MWD=$M_w/M_n$) and content of the monomeric units deriving from 1-hexene (1-hexene inserted).

Various polymerization tests were carried out with the above procedure, using the complexes prepared according to the previous examples 1 to 7. The conditions and results of the polymerizations are summarized in Table 1 below, in which, for each example, the zirconium complex is identified in the second column with reference to the respective preparation example.

which, for each example, the zirconium complex is identified in the second column with reference to the respective preparation example. Example 15 is reported for comparative purposes. The complex of formula (III), obtained according to example 1, gives lower activity and molecular weights than methyl substituted complexes, in ethylene omo-polymerization.

TABLE 2

| Ethylene polymerization | | | | |
|---|---|---|---|---|
| Example Number | 15 | 16 | 17 | 18 |
| Complex examp. nr. | 1 | 2 | 3 | 5 |
| SOL-CAT Conc. Zr (mg/l) | 42.0 | 45.7 | 40.2 | 88.2 |
| Zirconium (mg) | 0.063 | 0.033 | 0.032 | 0.032 |
| Al/Zr | 2600 | 2440 | 2510 | 2510 |

TABLE 1

| Ethylen/1-hexene polymerization | | | | | | | |
|---|---|---|---|---|---|---|---|
| Ex. nr | Complex Ex. nr | SOL-CAT Zr conc. (mg/l) | Zr (mg) | Yield (g polym.) | Activity ($g_{polym}/mg_{Zr} \cdot h$) | $M_W$ | MWD | 1-hexene inserted (mol %) |
| 8 | 1 | 48.6 (b) | 0.182 | 12.0 | 132 | 516,000 | 5.1 | 7.4 |
| 9 | 2 | 160.0 | 0.182 | 40.0 | 439 | 535,000 | 2.7 | 6.3 |
| 10 | 3 | 64.6 | 0.183 | 6.9 (a) | 151 | 661,000 | 3.8 | 4.8 |
| 11 | 4 | 156.0 | 0.182 | 14.1 (a) | 309 | 208,000 | 2.4 | 0.9 |
| 12 | 5 | 82.6 | 0.182 | 44.8 | 491 | 116,000 | 2.4 | 9.5 |
| 13 | 6 | 93.3 (c) | 0.182 | 17.2 | 189 | 650,000 | 3.7 | 1.0 |
| 14 | 7 | 186.2 | 0.182 | 6.7 | 147 | 447,000 | 4.1 | 10.5 |

(a) Polymerization time = 15 minutes
(b) SOL-CAT matured for 75 minutes at 50° C.
(c) SOL-CAT matured for 30 minutes at 40° C.

EXAMPLES 15–18 polymerization of ethylene

Various polymerization tests of ethylene were carried out corresponding to examples 15 to 18, using the following general procedure.

A solution of the polymerization catalyst (SOL-CAT) is prepared separately with the same procedure described in the previous example 8. 500 ml of toluene (previously distilled on metal sodium) and 0.54 ml of the above solution of MAO at 10% in toluene (0.848 mmoles of aluminium) are charged into the same BUCHI pressure-resistant reactor used in example 8 and conditioned as described above. The pressure-resistant reactor is heated to 70° C. and the desired quantity of the catalyst solution prepared as above is introduced with a syringe. The reactor is pressurized with ethylene to a pressure of 2 atms, and the polymerization is carried out for 30 minutes, continuously feeding ethylene so as to maintain the pressure constant for the whole duration of the test. The polymer is recovered by precipitation in acidified methanol and subsequent washings with acetone. The polymer thus obtained is linear polyethylene (HDPE) which is characterized by measuring the number average molecular weight ($M_n$) and the weight average molecular weight ($M_w$) and the molecular weight distribution (MWD= $M_w/M_n$).

Various polymerization tests were carried out with the above procedure, using the complexes prepared according to the previous examples 1 to 7. The conditions and results of the polymerizations are summarized in Table 2 below, in TABLE 2-continued

| Ethylene polymerization | | | | |
|---|---|---|---|---|
| Example Number | 15 | 16 | 17 | 18 |
| Yield (g of polymer) | 3.4 | 2.0(a) | 2.1(a) | 1.2 |
| Activity ($g_{polym}/mg_{Zr} \cdot h$) | 108 | 243 | 265 | 75.6 |
| $M_w/1000$ | 1790(b) | n.d. | n.d. | >2000(b) |

(a)Polymerization time = 15 minutes
(b)Values higher than the linear response range of the measuring instrument (a) Polymerization time=15 minutes
(b) Values higher than the linear response range of the measuring instrument

EXAMPLE 19 high temperature polymerization

The polymerization is carried out in a 1 liter, steel, adiabatic reactor capable of operating at 800–1200 bars and at temperatures of between 160° and 220° C. The average residence time is 40 seconds.

Two streams containing the monomers and catalyst solution respectively, are fed to the reactor continuously measuring the flow rate. The polymerization temperature and yield are controlled and regulated by the flow rate of the catalyst solution at a given temperature and composition of the gas, the flow of the catalyst decreases when its activity increases, so as to constantly maintain the yield of polymer, measured in continuous at the outlet of the reactor, within the range of 3–4 kg/h.

The catalyst solution is prepared by dissolving 562 mg (1.14 mmoles) of the complex prepared according to example 1 above, in 90 ml of toluene, and adding 150 ml of a solution of MAO in toluene (titer of Al=4.5M) (ratio Al/Zr=600). This solution is maintained under stirring at room temperature for about 1 hour, and is then diluted by adding 1800 ml of Isopar-L before being introduced into the reactor. The concentration of Zr in the solution fed is 0.507 mM. The stream containing the monomers consists of 64% of ethylene in volume and 46% of 1-butene. The polymerization temperature is maintained at a constant value of about 180° C. and the pressure is set at 800 bars and maintained by the continuous feeding of the monomers at the same pressure. An ethylene-butene copolymer is obtained having the following characteristics:

$M_n$=45.700; $M_w$=142.600; MWD=3.1;

Melt Flow Index (MFI)=0.45 g/19 min., density=0.9266 g/cm$^3$,

Short Chain Branching (SCB)=7.7/(1000 C atoms);

melting point=120.5° C., with a catalytic activity of 5.6 kg/mg$_{Zr}$.

EXAMPLE 20

(comparative)

The polymerization of ethylene and 1-butene is carried out with the same procedure described in example 19, with the commercial catalyst Et(Ind)$_2$ZrCl$_2$.

The catalyst solution is prepared by dissolving 220.4 mg (0.525 mmoles) of the above complex in 90 ml of toluene, and then adding 70 ml of a solution of MAO in toluene (4.5M) (Al/Zr=600). The mixture is maintained at room temperature for 1 hour and is then diluted with Isopar-L (1880 ml), obtaining a solution of the catalyst with a final concentration of Zr of 0.257 mM.

The polymerization is carried out feeding the catalyst in continuous, so as to maintain the temperature at 160° C. The gaseous stream consists of 45% in volume of 1-butene and 55% of ethylene, and is fed in continuous at 800 bars. The copolymer, obtained with a yield of 9.1 kg/mg$_{Zr}$, has MFI= 43.5 g/10 min., Mn=23.600, Mw=53.800, MWD=2.3, d=0.9269 g/cm$^3$, SCB=13.6/1000 C, m.p.=114.8° C.

EXAMPLES 21–24

Polymerization with Cationic Complexes

The complex of formula (IX), prepared according to example 7, is used for omo- and co-polymerizingethylene, in combination with a ionizing compound as component (ii) of the catalyst.

A solution of the polymerization catalyst was prepared separately, by first dissolving the desired quantity of complex (IX) in 50 ml of toluene in order to have a concentration of zirconium between 50 and 200 mg per liter of solution, and adding an amount of triethylaluminum (TEA) sufficient to reach the desired Al/Zr ratio. To this first solution, 25 ml of a toluene solution are added, containing dissolved therein an amount of a boron-containing ionizing compound (co-catalyst) such that the ratio B/Zr is equal to 1.0. The resulting mixture (clear and homogeneous) is matured by leaving it under stirring for 10 minutes at room temperature, before being introduced into the polymerization mixture. The compounds B(C$_6$F$_5$)$_3$ and [Ph$_3$C]+.[B(C$_6$F$_5$)$_4$]$^-$ are used as ionizing compounds.

Polymerization is carried out into a 1 liter BUCHI pressure-resistant glass reactor, which has been previously described in example 8. The reactor is thoroughly washed with 100 ml of a 0.1 molar solution of TEA, and filled with nitrogen before reaction. 470 ml of toluene (previously distilled on metal sodium), and eventually, for co-polymerization, 30 ml of 1-hexene (previously distilled on calcium hydride, CaH$_2$) are introduced. The pressure-resistant reactor is then pressurized with ethylene at 2 atms and heated at the reaction temperature.

The reactor is depressurized and the desired quantity of the catalyst solution prepared as described above, is introduced, in a stream of ethylene, The reactor is brought again to a pressure of 2 atms with ethylene and the polymerization is carried out for 10 minutes at the desired temperature, continuously feeding ethylene to maintain the pressure constant for the whole duration of the test. The polymer is recovered by precipitation in acidified methanol and subsequent washings with acetone and drying. The polymer is weighed and the reaction yield and catalyst activity is calculated. The conditions and results of the polymerization tests are summarized in Table 3 below.

TABLE 3

| Polymerization with cationic catalytic systems | | | | |
|---|---|---|---|---|
| Example Nr. | 21 | 22 | 23 | 24 |
| Conc. Zr in the reactor (M · 10$^6$) | 50 | 1.0 | 1.0 | 1.0 |
| Co-catalyst | B(C$_6$F$_5$)$_3$ | B(C$_6$F$_5$)$_3$ | [Ph$_3$C]$^+$. [B(C$_6$F$_5$)$_4$]$^-$ | [Ph$_3$C]$^+$. [B(C$_6$F$_5$)$_4$]$^-$ |
| Temperature (°C.) | 70 | 70 | 70 | 40 |
| Al/Zr | 10 | 500 | 500 | 500 |
| 1-hexene (ml) | — | — | — | 30 |
| Yield (g of polymer) | 14.2 | 4.1 | 7.3 | 3.1 |
| Activity (g$_{pol}$/mg$_{Zr}$ · h) | 38 | 540 | 975 | 410 |

EXAMPLE 25

Ethylene is polymerized under the same conditions as used according to examples 21–24 above, with a catalytic system constituted by the complex of formula (IX) (0.7 · 10$^{-6}$ mols/l) and MAO (Al/Zr=2500). 1.6 g of polyethylene are produced after 10 minutes reaction, with a catalyst activity of 300 (g$_{pol.}$/mg$_{Zr}$·h).

EXAMPLE 26

(comparative)

The polymerization of Example 22, above, is repeated with the same reagents and procedure, with the difference that complex of formula (IX) is replaced with the same molar amount of complex 1,2-ethylene-bis-($\eta^5$-indenyl) zirconiumdichloride. Only a few mg of polyethylene is formed after 10 minutes reaction, with a negligible catalyst activity.

We claim:

1. A catalyst for the (co)polymerization of ethylene and/or α-olefins comprising the following two components put in contact with each other:

(i) a metallocene complex having the following general formula (I):

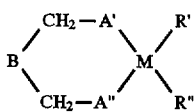

wherein: M represents a metal selected from the group consisting of titanium, zirconium and hafnium, A' and A" each independently represent an organic group containing a $\eta^5$-cyclopentadienyl anion co-ordinated to the metal M, R' and R" each independently represent an anionic group linked to the metal M;

B represents a divalent organic group comprising an unsaturated group linked to two —CH$_2$— methylene groups so that they form with this unsaturated group a rigid molecular structure, and the distance between the two —CH$_2$ methylene groups in the space is less than 3.5 Å;

(ii) a co-catalyst consisting of an organic compound of a metal M' selected from the group consisting of boron, aluminum, gallium and tin;

with the proviso that, when the groups A' and A" are both $\eta^5$-indenyl (C$_9$H$_7$), the divalent organic group B is different from ortho-phenylene.

2. Catalyst according to claim 1, wherein at least one of, A' and A" is $\eta^5$-indenyl substituted with from 1 to 7 methyl groups on the ring.

3. Catalyst according to claim 1 or 2, wherein at least one of, A' and A" is $\eta^5$-indenyl substituted with from 1 to 4 methyl groups on the 6 atom ring.

4. Catalyst according to claim 1, wherein said divalent organic group B consists of condensed aromatic groups in which the atoms linked to the two methylene groups of formula (I) are in "peri" position on two adjacent aromatic rings.

5. Catalyst according to claim 1, wherein said divalent organic group B consists of an olefinically unsaturated group characterized by the presence of a —C=C— group or a —C=N— group.

6. Catalyst according to claim 1, wherein component (ii) is an aluminoxane.

7. Catalyst according to claim 1, wherein component (ii) is an ionizing compound capable of transforming the metallocene complex of formula (I) into a cationic form active in polymerization and becoming a non-coordinating inert anion.

8. Catalyst according to claim 7, wherein the molar ratio between the ionizing compound and the complex of formula (I) is within the range of 0.3 and 10.

9. Catalyst according to either claim 7, further comprising, besides components (i) and (ii), an aluminum trialkyl or alkyl-halogenide, having from 1 to 8 carbon atoms in each alkyl.

10. Catalyst according to claim 7, wherein said aluminum trialkyl or alkyl-halogenide is in such a quantity that the molar ratio between Al and the metal M in the complex of formula (I) is comprised within the range from 10 to 1000.

11. The catalyst according to claim 1, wherein R' and R" each independently represent a group selected from the group consisting of hydride, halide, $C_1$–$C_{20}$ alkyl, $C_3$–$C_{20}$ alkylsilyl, $C_5$–$C_{20}$ cycloalkyl, $C_6$–$C_{20}$ aryl, $C_1$–$C_{20}$ alkoxyl, $C_1$–$C_{20}$ thioalkoxyl, $C_2$–$C_{20}$ dialkylamide and $C_4$–$C_{20}$ alkyl-silylamide.

12. The catalyst according to claim 2, wherein both A' and A" are $\eta^5$-indenyl substituted with from 1 to 7 methyl groups on the ring.

13. The catalyst according to claim 12, wherein both A' and A" are $\eta^5$-indenyl substituted with from 1 to 4 methyl groups on the 6 atom ring.

14. The catalyst according to claim 8, wherein the range is from 0.5 to 5.

15. The catalyst according to claim 8, further comprising, besides components (i) and (ii), an aluminum trialkyl or alkyl-halogenide, having from 1 to 8 carbon atoms in each alkyl.

16. The catalyst according to claim 14, further comprising, besides components (i) and (ii), an aluminum trialkyl or alkyl-halogenide, having from 1 to 8 carbon atoms in each alkyl.

17. The catalyst according to claim 10, wherein the range is from 100 to 500.

18. A process for the preparation of a co-polymer of ethylene and at least one α-olefin having at least 3 carbon atoms, comprising co-polymerizing ethylene and said α-olefin in suspension, solution or gas-phase, at a temperature from 0° to 250° C., and at a pressure of from 1 to 1200 atms in the presence of a catalyst including the following two components put in contact with each other:

(i) a metallocene complex having the following general formula (I):

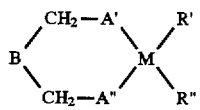

wherein:

M represents a metal selected from the group consisting of titanium, zirconium and hafnium, A' and A" each independently represent an organic group containing a $\eta^5$-cyclopentadienyl anion co-ordinated to the metal M, R' and R" each independently represent an anionic group linked to the metal M;

B represents a divalent organic group comprising an unsaturated group linked to two —CH$_2$— methylene groups so that they form with this unsaturated group a rigid molecular structure, and the distance between the two —CH$_2$ methylene groups in the space is less than 3.5 Å;

(ii) a co-catalyst consisting of an organic compound of a metal M' selected from the group consisting of boron, aluminum, gallium and tin.

19. A process according to claim 18, wherein said component (ii) is a polymeric aluminoxane, and the ratio between M in the compound of formula (I) and Al in the aluminoxane, ranges from 100 to 5000.

20. A process according to claim 18 or 19, wherein ethylene is co-polymerized with at least one α-olefin having from 3 to 8 carbon atoms, with a molar ratio of ethylene to said at least one α-olefin comprised from 0.05 to 10.

21. A process for the (co)polymerization of α-olefins, comprising polymerizing an α-olefin, or co-polymerizing a mixture of α-olefins, in suspension, solution or gas-phase, at a temperature above 100° C., and at a pressure of from 1 to 1200 atms, in the presence of a catalyst according to the definition given in the preceding claim 12.

22. Process according to claim 21, wherein said group B in the complex compound of formula (I) is an aromatic group.

23. A process for the (co)polymerization of α-olefins, in suspension, at low, medium or high pressure and at temperatures of between 50° and 240° C., or in solution in an inert diluent operating at pressures of between 10 and 150 bars and temperatures of between 120° and 230° C., or in gas-phase, with temperatures within the range of 60° to 160° C., at pressures of between 5 and 50 bars, wherein an α-olefin or a mixture of α-olefins is made to polymerize in the presence of a catalyst according to anyone of claims 1 to 10 or claims 18 to 24.

24. The process of claim 18, wherein the α-olefin has 3 to 12 carbon atoms.

25. The process of claim 18, wherein the pressure is from 50 to 300 atms.

26. The process of claim 24, wherein the pressure is from 50 to 300 atms.

27. The process of claim 21, wherein the temperature is from 150° to 240° C.

28. The process of claim 21, wherein the pressure is from 500 to 1200 atms.

29. The process of claim 27, wherein the pressure is from 500 to 1200 atms.

* * * * *